United States Patent [19]
Cook

[11] Patent Number: 5,263,973
[45] Date of Patent: Nov. 23, 1993

[54] SURGICAL STAPLING METHOD

[76] Inventor: Melvin S. Cook, 8 Saddle Ridge Rd., Hohokus, N.J. 07423

[21] Appl. No.: 934,858

[22] Filed: Aug. 24, 1992

Related U.S. Application Data

[63] Continuation-in-part of Ser. No. 753,116, Aug. 30, 1991, Pat. No. 5,179,964.

[51] Int. Cl.5 .............................................. A61B 17/00
[52] U.S. Cl. .................................... 606/216; 606/215; 606/219; 606/220
[58] Field of Search ............... 606/215, 216, 217, 219, 606/220; 128/898

[56] References Cited

U.S. PATENT DOCUMENTS

| | | | |
|---|---|---|---|
| 2,472,009 | 5/1949 | Gardner | 606/216 |
| 2,669,747 | 2/1954 | Detaranto | 606/216 |
| 3,068,869 | 12/1962 | Shelden et al. | 606/216 |
| 3,166,072 | 1/1965 | Sullivan . | |
| 3,385,299 | 5/1968 | Le Roy . | |
| 3,625,220 | 12/1971 | Engelsher . | |
| 4,201,215 | 5/1980 | Crogsett et al. . | |
| 4,467,805 | 8/1984 | Fukuaal . | |
| 4,637,380 | 1/1987 | Orejola | 606/216 |
| 4,676,245 | 6/1987 | Fukuda | 606/216 |

FOREIGN PATENT DOCUMENTS

| | | |
|---|---|---|
| 0192443 | 2/1988 | European Pat. Off. . |
| 0380025 | 8/1990 | European Pat. Off. . |
| 8203058 | 10/1982 | France . |

Primary Examiner—Stephen C. Pellegrino
Assistant Examiner—Gary Jackson
Attorney, Agent, or Firm—Kaplan and Mugno

[57] ABSTRACT

An improved surgical stapling method and apparatus therefor is disclosed in which parallel rows of staples are inserted prior to forming an incision. When the incision is to be closed, the corresponding staples of the two rows are brought together by suitable locking pins or other techniques.

3 Claims, 4 Drawing Sheets

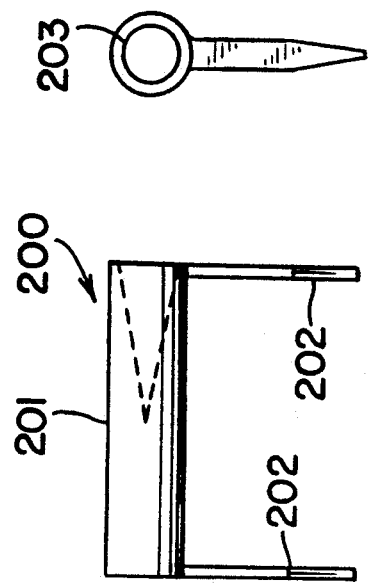
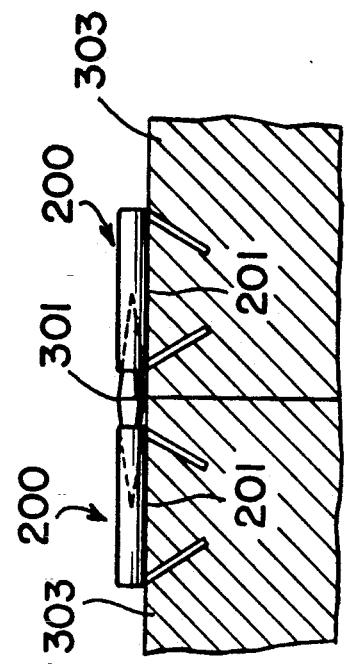
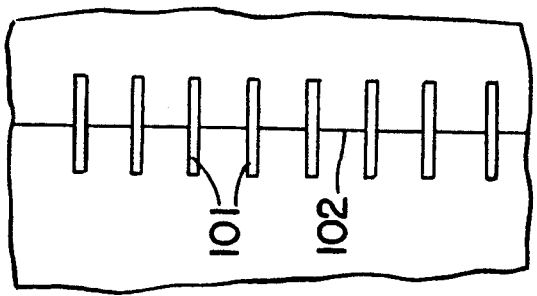
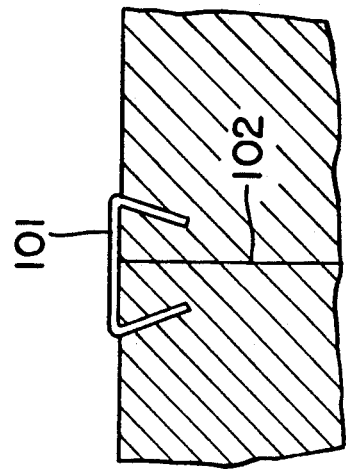
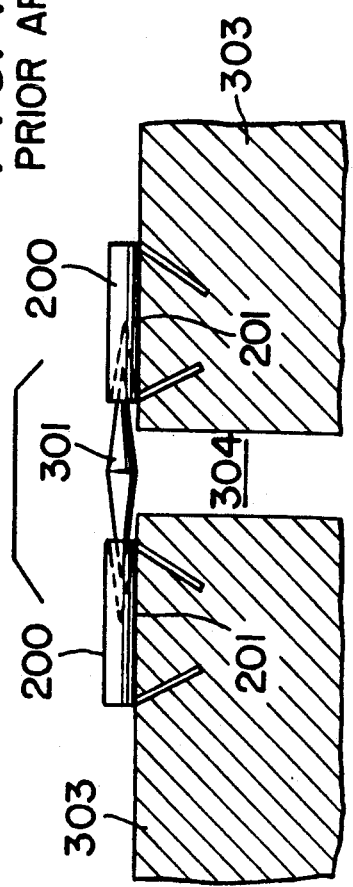

SURGICAL STAPLING METHOD

RELATED APPLICATION

This application is a continuation in part of co-pending U.S. patent application Ser. No. 753,116 filed Aug. 30, 1991, now U.S. Pat. No. 5,179,964.

TECHNICAL FIELD

This invention relates to surgical stapling, and more particularly, to an improved method of surgical stapling to reunite severed tissue.

DESCRIPTION OF THE PRIOR ART

Surgeons can close an incision and reunite severed tissues by using staples or stitches. The use of staples is usually faster and easier than is the use of stitches. For example, when a long incision is made in a patient's leg in order to then remove a vein for use in open heart surgery, the incision may be closed by stapling.

FIG. 1 shows a cross-sectional view of an implementation of a typical prior art surgical stapling method. Incision 102 is made in tissue 103 enabling a surgical procedure to be performed. To close the incision, tissue from each side of the incision is brought together. The two legs of staple 101 are then inserted into opposite sides of the incision, as shown, so that the bridge (crown) of the staple 101 holds the severed tissue together, and the incision is thereby closed in the local region of the staple. Staples, each of which is shaped like staple 101, are sequentially inserted along the length of the incision to close it, as shown in FIG. 1A.

While this prior art stapling procedure is typically faster and easier than stitching, it is difficult to accurately align the tissue during stapling. Specifically, the surgeon brings together tissue from both sides of an incision, e.g., with hooks or by pressing the tissue together, and then inserts a staple. This is repeated along the length of the incision. Frequently, as a result of the limitations of the techniques, severed tissue is rejoined with an alignment and conformation that does not accurately reproduce the pre-existing alignment and conformation. As a result, after reuniting and healing, the tissue may be distorted and a large and unsightly scar may develop. Further, since scar tissue may shrink, depressions can form as time progresses. Less scar tissue and shorter healing times would result if the tissue was reunited more precisely.

Thus, a problem remaining in prior art stapling is to provide a method of rejoining severed tissues which is quick and easy but which does not result in large unsightly scars and minimizes distortions and scar tissue.

SUMMARY OF THE INVENTION

It is an object of the invention to provide a surgical stapling method which improves alignment of rejoined severed tissue in order to minimize the scar tissue formed during healing.

It is another object of the invention to provide a method of surgical stapling that minimizes the time required for healing of incisions.

It is another object of the invention to provide a method of surgical stapling that minimizes distortions of reunited tissue.

These and other objects are achieved with the present invention, which provides a method of surgical stapling that utilizes two or more parallel rows of staples inserted in tissue. In the preferred embodiment, two parallel rows of staples are inserted into tissue. An incision between the parallel rows of staples allows the surgical procedure to be performed. When the severed tissue is to be reunited, two staples—one staple from each of the two rows—are joined to each other. These two staples are herein termed "corresponding staples" or a "corresponding staple pair", and when they are joined and locked to each other, the incision in the local region of the corresponding staples is closed thereby. When the corresponding staples along the entire length of the incision are locked together, the incision is closed.

In a preferred embodiment, staples are inserted into tissue in pairs, i.e., the two staples comprising a corresponding staple pair are simultaneously inserted, preferably prior to or at the time the incision is made, although the staples may be inserted subsequent to forming the incision. Thus, corresponding staples have orientations and locations that are characteristic of the conformation of the tissue prior to its being severed. When corresponding staples are locked together, the severed tissue is rejoined with a conformation characteristic of the conformation that existed prior to being severed. A tool is also provided for simultaneously inserting a corresponding staple pair and for severing tissue therebetween.

BRIEF DESCRIPTION OF DRAWINGS

FIG. 1 shows a staple as utilized in the prior art to join severed tissue;

FIG. 1A shows a surgical incision closed via a plurality of prior art staples;

FIG. 2A shows a cross-sectional view of a staple which may be used to implement the inventive method;

FIG. 2B depicts a side view of the staple of FIG. 2A;

FIG. 3 shows 2 staples which are inserted into tissue and are arranged to implement the inventive surgical stapling method;

FIG. 4 shows a cross-section of a portion of tissue which has been rejoined utilizing the inventive method;

FIG. 6A shows an alternative scalpel which may form an incision to be closed utilizing the inventive stapling method;

DETAILED DESCRIPTION OF THE PREFERRED EMBODIMENT

Figures 5, 7A, 7B:
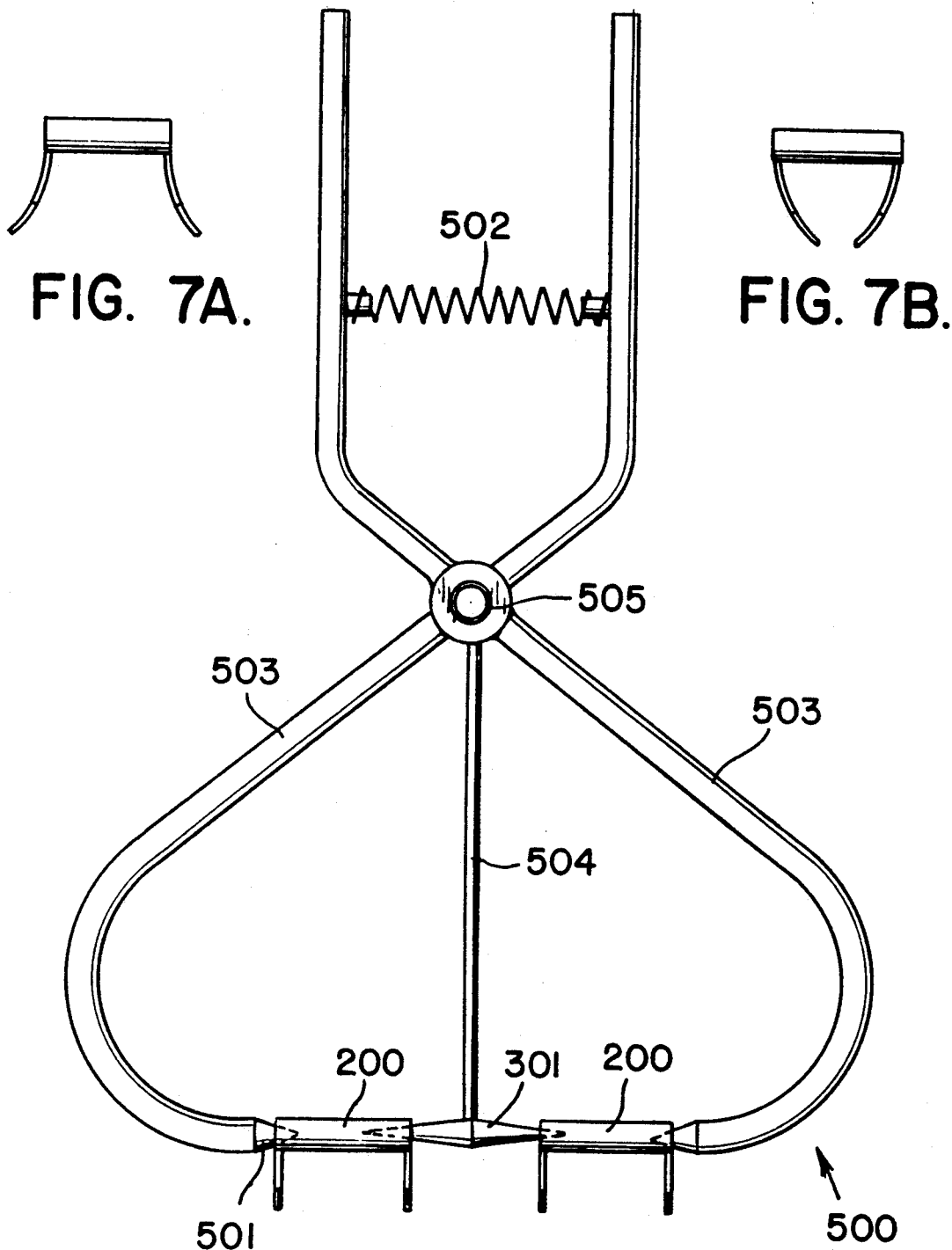
FIG. 5 shows a locking tool which may be utilized in accordance with the teachings of the present inventions.
FIG. 7A shows an exemplary prong shape to be utilized with the staples discussed hereafter.
FIG. 7B shows yet another staple prong shape which may be utilized to implement the stapling technique described hereafter.

FIG. 2A shows a staple 200 including crown 201 and legs 202 which may be used for implementing the present invention. The crown 201, unlike the crown of a typical prior art staple, has a hollow recess which may extend partly into or through the crown. The recess allows insertion of a locking pin therein, as will be explained hereafter. The staples used in the present invention can be smaller than those used in prior art stapling as two staples are employed where one was used. A possible crown width of 6 mm between legs and a leg (prong) length of 4 mm is suggested but other staple dimensions are, of course, within the scope of the invention. FIG. 2B shows a side view of the staple 200. Bore 203 is shown as circular in cross-section although it may have a variety of other cross-section shapes e.g., rectangular or oval.

FIG. 3 shows a cross-section of two staples 200 that could be used to close an incision locally in accordance with the present invention. The two staples form a corresponding staple pair and are inserted on opposite sides of incision 304, preferably before or when such incision was locally made. To reunite the severed tissue locally, the two staples are pushed towards each other as a double-tapered locking pin 301 is inserted into recesses in the crowns of the staples, as shown in FIG. 3. The pin locks into the recesses, and the two staples are thereby locked together. This rejoins the severed tissue in the local region. As the pair of staples have an orientation and location characteristic of the tissue prior to being severed, the orientation of the rejoined tissue is characteristic of that of the tissue prior to its being severed.

A somewhat different embodiment of the two staples of a corresponding staple pair can be used, where the two staples are locked together by means of an extension jutting out from the crown of a first one of the two staples. When the two staples are joined together, this extension enters a recess in the crown of the second staple and locks into it. Other staple configurations are also possible, e.g., where the two staples look like prior art staples but are locked together by a member that grasps the crowns of the two staples, the essential feature being that the two staples forming a pair of corresponding staples are locked together and held in a position which, in turn, helps to join the local severed tissue with an orientation which reproduces its original orientation. Naturally, more than two staples can be locked together simultaneously if such is desired.

FIG. 4 shows a cross-section similar to that of FIG. 3 wherein the staples 200 are brought together and locked in place via the locking pin. In dotted outline, the locking pin is shown within the recesses in the staple crowns 201. As can be seen from FIGS. 3 and 4, as the staples are brought towards each other, the locking pin 301 enters the recesses in the proximate ends of the crowns 201 of the staples and engages the surfaces of the recesses, thereby locking the staples to each other. To facilitate such locking, the pin 301 preferably has a double-tapered shape with the central portion of the pin being thicker than its ends and having a diameter equal to or larger the diameters of the proximate ends of the recesses 200 in the crowns 201 of the staples. Thus, as the staples 200 are brought towards each other, eventually the tapered pin 301 engages the surfaces of the recesses and is locked and retained thereby. If the crowns of the staples have slits along their length, their separations can be varied and the surgeon will be able to adjust the separations of the corresponding staple pairs with respect to each other so as to optimize the reuniting of the severed tissue. To close the entire incision, the surgeon proceeds along the double row of staples and sequentially locks the staples of corresponding staple pairs together along the length of the incision.

Corrugations on the pins and/or the surfaces of the recesses in crowns 201, or splits along the crowns 201 along its length as suggested above, can assist locking the pins in the recesses. Protuberances can be formed on a pin, i.e., "stop-ridges", to establish a predetermined separation of the pair of staples connected by the pin. Alternatively, as the two staples of a corresponding staple pair are brought towards each other by the surgeon, he can establish the separation desired for the connected corresponding staples to develop optimum local rejoining of the severed tissue by ceasing to push the staples towards each other when the desired result is achieved.

FIG. 5 shows a locking tool 500 which may be used for joining two staples while inserting a locking pin when it is desired to close an incision. Two exemplary staples 200 are shown in FIG. 5, the staples 200 being positioned so as to be brought together by use of the locking tool 500. Locking tool 500 includes a pair of arms 503 connected by a bolt 505 around which they can rotate, and also includes a locking pin holder 504 extending from said connection and mounted in such a manner that it can rotate independently of said pair of arms 503. In other words, as the arms 503 move towards each other, the position of the locking pin holder 504 is independent of the positions of the arms 503. Locking tool 500 further includes spring 502 for biasing arms 503 and also includes prongs 501 for pushing the pair of staples towards each other to lock them onto the locking pin held by the locking pin holder 504.

As can be seen from FIG. 5, when using the locking tool 500, the surgeon inserts the prongs 501 into the distal ends of the staples to be locked together and closes locking tool 500 by brings arms 503 towards each other by squeezing the locking tool 500 with his hand and thereby compressing spring 502. When the two staples are locked together by the locking pin, the surgeon releases his grip and spring 502 pushes on arms 503 and releases the prongs 501 of the locking tool 500 from the staples. Optionally, the locking pin may be replaced by an extension of one of the staples of a corresponding staple pair that enters and is locked into the crown of the other staple of the pair, and in such case, a locking pin holder is not necessary. Moreover, a more complex tool may include more than one pair of arms 503 operating in parallel so that more than one corresponding staple pair can be simultaneously locked together. Further, locking pins may be stored in the tool and fed out by an optional locking pin storage and feed mechanism similar to that used in typical staplers to store and feed staples.

In accordance with the above description, it can be seen that the invention allows tissue on opposite sides of the incision to be aligned more accurately as far as their original configuration is concerned than generally occurs with prior art techniques. This is so since the staples of the corresponding staple pairs are inserted when the tissue has its original conformation, and thus their orientation is characteristic of the original tissue conformation, so that when they are joined and locked together, tissue are realigned in a manner characteristic of the original tissue conformation. Naturally, since they are pressed together at the incision, there will be some deviation from the original conformation, but this deviation typically is substantially less than occurs in prior art surgical stapling techniques.

It should be noted that while the locking pins and the recesses into which they are inserted have been shown as being circular in cross-section, it may be desirable to make these cross-sections non-circular, e.g., rectangular, elliptical, oval, or of other noncircular shape. Such non-circular shape prevents the staples from rotating relative to each other before or after they are joined.

This helps to produce more exact alignment of the rejoined tissue. On the other hand the surgeon may prefer the greater latitude allowed him with the use of staples and locking pins with the circular cross-sections sections since he can adjust the tissues more easily as they are rejoined.

When the crown contacts the underlying tissue, this minimizes subsequent movements of the staple with respect to the tissue. Furthermore, if the bottom of crown 201 in contact with the tissue has a flat surface which rests on the tissue when the staple is inserted, this further minimizes possible movements of the staple with respect to the tissue.

The legs of the staples may be preformed to the shape desired when they are inserted in the tissue, i.e., shaped before the insertion process, or the legs may be shaped during staple insertion by use of an anvil (staple leg shaping device). If the staples are preshaped, it is not essential but it is helpful to use staples made, at least in part, of resilient material so that the legs can be bent and yet return to the desired shape in the tissue as they are inserted. Optimally, staple legs move during the insertion process such that the holes formed in the tissue as they penetrate remain as small as possible in order to minimize bleeding and to help retain the staples in the desired positions. Staple leg lengths must be sufficient to hold the staples in place when corresponding staples are connected.

It is desirable that the stapling device used to insert the staples into the tissue is simple in construction and light in weight. Preferably, it is also inexpensive so that it can be discarded after use, thus avoiding the necessity to be disassembled, sterilized and reassembled after use.

Two possible staple leg conformations are shown in FIG. 7. In FIG. 7(a), the legs of the staple are spread apart. In FIG. 7(b) the legs of the staple are bent towards each other. The leg conformations shown in FIG. 7(b) is usually preferred as superior for the purpose of surgical stapling than those shown in FIG. 7(a).

Stapling devices usually require one or more staple pushers and one or more leg spacing devices to establish the desired staple leg conformations as the staples are inserted into tissue. A leg spacing device can be part of anvil structure, i.e., a leg shaping device, if the staple legs are not pre-shaped.

Figure 6:
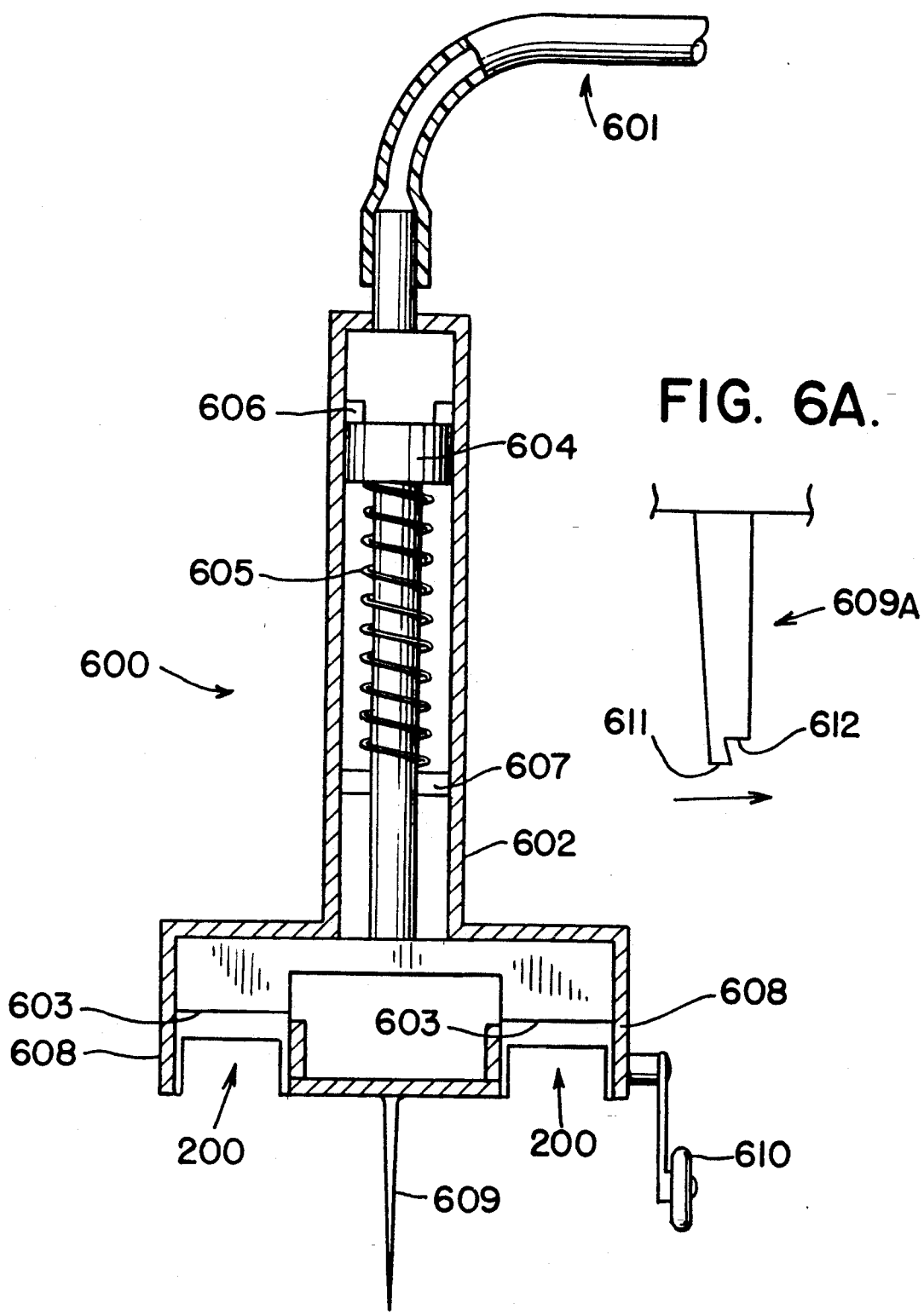
FIG. 6 shows a combination scalpel/stapler which also implements the inventive methods.

FIG. 6 shows an embodiment of the invention which allows a surgeon to conveniently insert a corresponding staple pair while simultaneously forming part of the incision between the staples. Surgical tool 600 receive pulses of gas, e.g., air or nitrogen, under pressure from a compressed gas source 601. The source 601 may include, e.g., a pump or a cylinder of compressed gas, and provides pulses of compressed gas which push on piston 602 and cause the piston to oscillate. The pulses of compressed gas can be delivered at some pre-determined rate, e.g., once per second, or alternatively, delivery of the pulses can be under the control of the surgeon, e.g., by use of a foot pedal.

In operation, a pulse of compressed gas provided by source 601 increases the gas pressure above piston top 604. This forces piston 602 down. Piston bottom 603, via a mechanical linkage, acts against the top of staples 200. The staples are located in shafts 608, as shown. The staples are forced out of surgical tool 600 and inserted into tissue under the tool. Not shown in FIG. 6 is a leg shaping device, but such devices are well-known in the art.

At the end of the pulse of compressed gas, gas pressure is released above the piston 602 and spring 605 forces the piston up until piston top 604 encounters piston stop 606 and has thus returned to the position it was in before the arrival of the pulse of compressed gas. Spring stop 607 retains one end of spring 605 in position, as shown in FIG. 6. As piston 602 returns to its original position, two staples are fed into shaft 608 so they are ready to be inserted during the next cycle of operation of the tool. Typical spring-loaded staple holders (not shown) such as are well-known in the art can be used to store and feed staples.

Also shown in FIG. 6 is an optional knife blade 609 which can be used to sever tissue as staples are being inserted. Blade 609 can be a conventional surgical scalpel blade, for example, mounted on the bottom of the tool so that it cuts between the staples inserted in the tissue. A device that monitors the length of the incision, e g., a small wheel 610 which contacts the tissue, can be used to determine the separation between adjacent corresponding staple pairs.

FIG. 6A shows an expanded view of an optional improved surgical blade 609A which may be used with the invention. Blade 609A, unlike blade 609, is powered to reciprocate in a direction generally orthogonal to the direction of the length of the incision. It severs tissue in the direction it moves. Blade 609A may be mechanically linked to the piston 602, for example, and be driven into the tissue as a result of the motion of the piston. However, blade 609A may be driven by alternative methods, as will be obvious to one skilled in the art.

As blade 609A pushes into tissue, two portions of an incision are thereby created; a deeper portion by edge 611 and a shallower portion by edge 612. As blade 609A is moved in the direction along the length of the incision, the blade 609 A reciprocates. The portion of the incision made by edge 612 is then made deepened by the edge 611 during the successive motion of the blade 609A, while edge 612 creates a new portion of the incision. This, as blade 609A moves along the length of the incision, edge 611 deepens the shallow cuts made edge by 612 while edge 612 makes shallow cuts which will be deepened by edge 611. The result is that the desired depth of cut is made while the necessary vertical motion of blade 609A is reduced. An extension (leg) may be attached to the rear of the surgical tool to separate the severed tissue so that multiple parallel cuts which would increase bleeding are not made.

A reciprocating blade such as blade 609A, whether multiple edges are used or not, has the advantages that the depth of the incision can be more precisely controlled than with a conventional knife-type scalpel and that tissues that are both softer or harder than those easily severed by a conventional knife-type scalpel can be severed by blade 609A.

Figure 8:
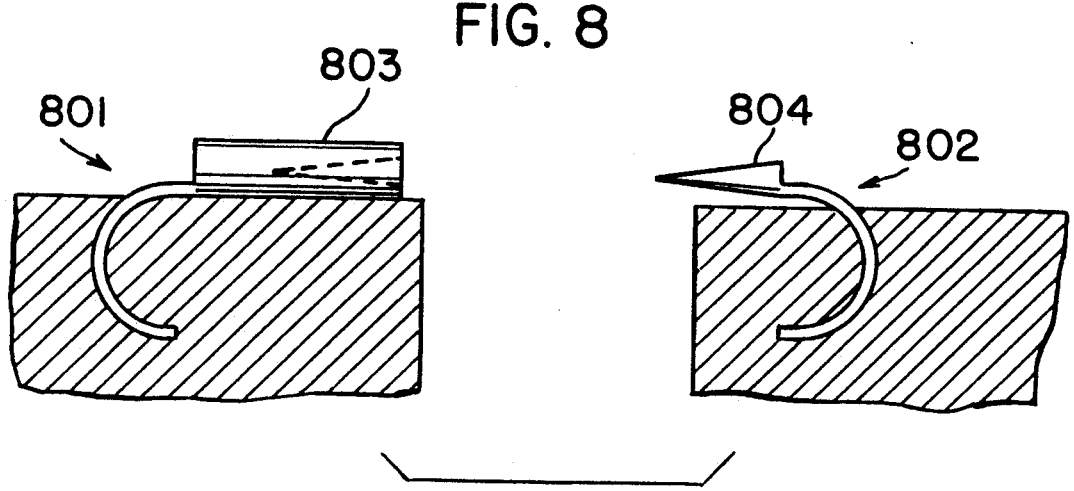
FIG. 8 shows an alternative type of staple for use with the invention.

FIG. 8 shows an additional possible embodiment of the present invention. The half staples 801 and 802 are utilized, rather than full staples. The half staples may be inserted after the incision has been made, during the time that the incision is being made, or prior to the making of the incision. One such half staple is located on each side of the incision to be made or to be closed. When connected to each other, two associated half staples 801 and 802 form a connected staple with two legs. Preferably, associated half staples are inserted into the tissue after the surgical procedure and when the incision is to be closed. The actual connection can be made by various means, as for example, by methods shown in the prior U.S. patent application Ser. No. 07/753,116. Another technique shown in FIG. 8 for connecting the half staples is that one of the half staples 801 can have a hollow socket 803 forming part of its crown, and the other associated half staple 802 can have a prong 804 which enters and is retained by the hollow crown 803.

When half staples are connected, the resulting staple must be held firmly in place by the tissues into which the connected staple is inserted so that the incision is held closed and healing can take place. Such half staples can be inserted while causing less distortion of the underlying tissue than is the case with typical prior art surgical staples since only one leg need be inserted and thus the requirement that a second leg be inserted simultaneously is not necessary. Each half staple should can have a leg shape such that when two associated half staples are connected, the resulting connected staple is held firmly in place by the tissue. This may require that the legs be bent after insertion or after connection to achieve a B-shape, such as is well known in the art, for the connected staple. (This may also be done for full staples.) Such bending of legs is optional and may be accomplished by exerting forces on the legs while holding the crowns of the staples or half staples, as is well known in the art. Alternatively, if the legs of a staple or half staple are formed of a resilient material, e.g., one of the spring-type steels, the staple can be bent during insertion and then allowed to relax so as to achieve a leg configuration for the connected half staple or for individual staples to have the desired B-shape. If the legs have an oval or circular shape during insertion, distortion of the tissue will be less if the legs are subsequently bent than is the case in the prior art whereby staples with two straight legs are inserted and the legs then bent to achieve a B-shape for the inserted staple.

It is also noted that the tissue may be perforated by the stapler or another instrument prior to the insertion of a staple or a half staple, with the leg or legs of the half staple or staple then being pushed into the perforation thus made. When this is done, the end of the leg is preferably rounded or smoothed so that it slides into the perforation and does not create a new hole. This is helpful in minimizing tissue distortion, scar tissue formation, and healing time.

The tissue may be marked with lines drawn orthogonal to the area where the incision is to be made, e.g. with a dye or ink, prior to making of the incision or emplacing staples or half staples. When the incision is to be closed, these lines can be aligned and staples inserted using the lines as guides so that the severed tissue is reunited with a conformity that is close to that existing prior to the making of the incision.

Additionally, these staples may be intermixed with prior art staples.

In performing anastomosis, i.e. surgical connection of separate or severed hollow organs, the ends of the organs joined can be everted or inverted at the union. If the connection is not well made, leakages of food, blood, feces, and the like can occur at the imperfect union. This can be severely detrimental to the patient. In prior art stapling techniques, it is sometimes difficult to avoid such problems where the thickness of the organs at the union sites varies. Further, in prior art stapling techniques, it is often necessary to make stab wounds in the organs to be joined so that the jaws of the stapler can reach the site to be stapled. Such stab wounds must subsequently be closed and thus complicate and prolong the procedure as additional damage to the patient.

Figure 9:
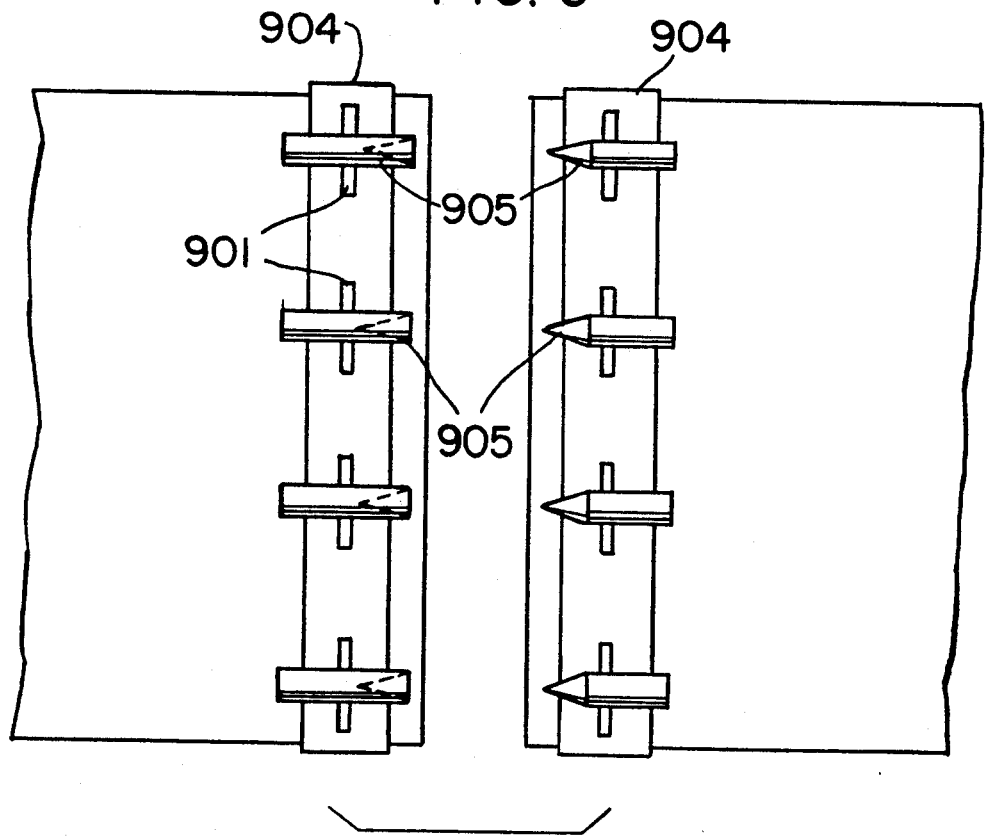
FIG. 9 shows still another embodiment of the invention which may be used for anastomosis.

In a further embodiment of the present invention, associated staples are connected after being inserted and the connection is utilized in anastomosis. An exemplary arrangement for accomplishing the purpose in accordance with the present invention is shown in FIG. 9. A strip of tape 904 bearing half staples or staples 901 attached on each of the two hollow organs to be joined. The half staples or staples on each of these two tapes are located at predetermined separation intervals from the adjacent half staples or staples on each tape, and these separation intervals are identical on each tape. As the tapes are attached before the union is made, access for the stapler does not require additional stab wounds to be made for the purpose of stapler access to be the stapling sites. The staples or half staples may be oriented with their crowns being substantially parallel to the union cite as shown in FIG. 9. On the crown of each of the staples is a connection means 905 which may be of the type previously described herein for example. Only several of the staples and connection means of FIG. 9 are labelled, for clarity. When the staples or half staples on one of the tapes are connected to the associated staples or half staples on the other one of the tapes, the union is made. Since the staples or half staples are located at predetermined separation intervals, the union can be made without leakages occurring.

The technique allows anastomosis to be performed quickly and easily. The tapes can be made of materials substantially inert and biologically well-tolerated by patients. Preferably, these materials are eventually absorbed. If the tape materials have some thickness and resiliency, it is helpful in avoiding necrosis of underlying tissue while still enabling leakages at the union site to be avoided.

Having described the preferred embodiment of the invention, it can be seen that various other modifications and/or additions will be obvious and apparent to those of ordinary skill in the art. For example, while pointed locking pins have been shown, it is readily apparent that other means may be used to connect associated staples or half staples such as, for example, clips, wire, or locking pins with blunt ends. Finally, it should be noted that associated staples or half staples such as are disclosed herein may be used for purposes other than surgery such as, e.g. joining hardware and other articles.

I claim:

1. A method of joining tissue at an incision site comprising the steps of:
   inserting a plurality of half staples on each side of said incision in said tissue, each of said half staples having an associated half staple on the other side of said incision;
   forming connections of said associated half staples, said connections being such that the separation of said associated half staples is continuously variable, said step of forming comprising the step of inserting a prong from one staple into a hollow crown on another staple.

2. The method of claim 1 further comprising the steps of marking the incision site with markings prior to making said incision and placing said half staples along corresponding markings after said incision is complete.

3. A method of joining tissues at an incision comprising the steps of:
  inserting a plurality of staples on each side of an incision into said tissues, said staples being arranged along and perforating through strips of tape, each of said staples having an associated staple on the other side of said incision and including connection means;
  forming connections of said associated staples, said connections being such that the separation of said associated staples is continuously variable.

* * * * *